(12) United States Patent
Goldstein et al.

(10) Patent No.: US 8,311,228 B2
(45) Date of Patent: Nov. 13, 2012

(54) EAR INPUT SOUND PRESSURE LEVEL MONITORING SYSTEM

(75) Inventors: Steven W. Goldstein, Delray Beach, FL (US); John Usher, Montreal (CA); Brian Fligor, Mansfield, MA (US)

(73) Assignee: Personics Holdings Inc., Boca Raton, FL (US)

( * ) Notice: Subject to any disclaimer, the term of this patent is extended or adjusted under 35 U.S.C. 154(b) by 1300 days.

(21) Appl. No.: 11/757,152

(22) Filed: Jun. 1, 2007

(65) Prior Publication Data

US 2008/0037797 A1   Feb. 14, 2008

Related U.S. Application Data

(60) Provisional application No. 60/887,165, filed on Jan. 30, 2007, provisional application No. 60/803,708, filed on Jun. 1, 2006.

(51) Int. Cl.
*H04R 29/00* (2006.01)
*G01H 3/10* (2006.01)
*G01H 3/14* (2006.01)
*A61F 11/06* (2006.01)

(52) U.S. Cl. ............. 381/56; 381/71.6; 381/72; 73/646

(58) Field of Classification Search ............ 381/56, 381/57, 71.6, 71.8, 72; 600/25; 73/585, 73/645, 646
See application file for complete search history.

(56) References Cited

U.S. PATENT DOCUMENTS

| | | | |
|---|---|---|---|
| 3,802,535 A * | 4/1974 | Peake et al. | ........... 73/646 |
| 3,987,245 A | 10/1976 | Fasen | |
| 4,554,639 A * | 11/1985 | Baker et al. | ........... 73/647 |
| 4,947,432 A | 8/1990 | Topholm | |
| 5,430,826 A | 7/1995 | Webster | |
| 5,692,059 A | 11/1997 | Kruger | |
| 5,757,930 A | 5/1998 | Seidemann | |
| 6,379,314 B1 | 4/2002 | Horn | |
| 6,456,199 B1 | 9/2002 | Michael | |

(Continued)

FOREIGN PATENT DOCUMENTS

EP    165468 A1    12/1985

(Continued)

OTHER PUBLICATIONS

Osha, "Occupational Noise Exposure", Jul. 1, 2005, Section 1910.95, pp. 211-223.

(Continued)

*Primary Examiner* — Jesse Elbin

(74) *Attorney, Agent, or Firm* — RatnerPrestia

(57) ABSTRACT

Systems and methods for monitoring a sound pressure level dose at an ear are provided. A system includes an audio transducer which outputs a sound signal is placed within an ear to receive sound at the ear. A sound level threshold detector determines whether a sound pressure level of the sound signal is at a minimum level and outputs a sound pressure level signal corresponding to the sound pressure level when the sound pressure level is not at the minimum level. A time period is calculated during which the sound pressure level is not at the minimum threshold level. A listening fatigue calculator determines whether a cumulative effect of exposure to the sound signal at the ear over the time period will cause harm to the ear. At least a portion of the system is disposed in situ at the ear.

20 Claims, 7 Drawing Sheets

U.S. PATENT DOCUMENTS

| | | |
|---|---|---|
| 6,473,512 B1 | 10/2002 | Juneau |
| 6,648,820 B1 | 11/2003 | Sarel |
| 6,754,359 B1 * | 6/2004 | Svean et al. .................. 381/328 |
| 6,826,515 B2 | 11/2004 | Bernardi et al. |
| 6,840,908 B2 | 1/2005 | Edwards |
| 7,756,281 B2 | 7/2010 | Goldstein |
| 2003/0165246 A1 | 9/2003 | Kvaloy |
| 2005/0020873 A1 | 1/2005 | Berrang et al. |
| 2005/0117765 A1 | 6/2005 | Meyer et al. |
| 2005/0250439 A1 | 11/2005 | Leslie |
| 2005/0254665 A1 | 11/2005 | Vaudrey |
| 2005/0254667 A1 | 11/2005 | Michael |
| 2006/0137934 A1 | 6/2006 | Kurth |
| 2007/0129828 A1 | 6/2007 | Lee |
| 2007/0147624 A1 * | 6/2007 | Fischer ........................ 381/23.1 |
| 2007/0270988 A1 | 11/2007 | Goldstein |
| 2008/0194984 A1 * | 8/2008 | Keefe ............................. 73/585 |

FOREIGN PATENT DOCUMENTS

| | | |
|---|---|---|
| EP | 1615468 A1 | 1/2006 |
| WO | 2006002055 A2 | 1/2006 |
| WO | WO2006/002055 A2 | 1/2006 |

OTHER PUBLICATIONS

Office Action for U.S. Appl. No. 11/931,252, mailed Jul. 19, 2011.

* cited by examiner

EAR INPUT SOUND PRESSURE LEVEL MONITORING SYSTEM

CROSS-REFERENCE TO RELATED APPLICATIONS

This Application is a Non-Provisional and claims the priority benefit of Provisional Application No. 60/803,708 filed on Jun. 1, 2006 and Provisional Application No. 60/887,165 filed on Jan. 30, 2007, the disclosures of which are incorporated herein by reference in their entirety.

BACKGROUND OF THE INVENTION

This invention is directed to a system for monitoring the sound pressure levels at a listener's ear, and in particular, thought not exclusively, monitoring the sound pressure levels over time and to utilize that information to reduce hearing damage.

With the advent of an industrial society, people are exposed to noise pollution at greater and greater levels; both from background, such as street traffic, airplanes, construction sites and intentional exposure to high sound levels such as cell phones, MP3 players, and rock concerts. Studies show that ear damage, leading to permanent hearing impairment is not only increasing in the general population, but increasing at a significantly faster rate in younger populations.

The potential for hearing damage is a function of both the loudness and the duration of exposure to the sound stimulus. Safe listening durations at various loudness levels are known, and can be calculated by averaging audio output levels over time to yield a time-weighted average. Standard guidelines published by OSHA, NIOSH or other agencies are known. This calculation can be even further improved by accounting for aspects of the playback scenario, specifically the characteristics of the sound source and their proximity to the listener's ear.

Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise. Background noise canceling earphones such as those produced by Bose and others, attempt to protect the ear form excessive ambient noise by producing a counter noise wave to cancel out the ambient noise at the ear. These prior art devices have been less than satisfactory because they do not completely prevent high decibel noise from reaching the ear, and do not account for the duration of exposure to harmful sounds at the ear.

It is also known from the prior art to provide active noise reduction at the ear to protect the ear from exposure to loud noises as disclosed in U.S. patent Application No. US2005/0254665. The art actively attenuating noise reaching the inner ear utilizing a control; a connection with an earpiece and attenuating the noise to the ear. However, there is no monitoring of the noise over time to account for the cumulative effect. Furthermore, there is no accounting for any restorative effects for sound pressure levels which are healing to the ear rather than destructive.

Dosimeters, such as that described in U.S. published Application No. US2005/0254667 are known. The device periodically measures prior sound level within the ear canal. However, the device does not take into account the cumulative effect of the noise or the effect of any restorative period. Furthermore, no remedial action is taken as a result of the readings.

It is also known from the prior art that headphones for consumer electronics have been provided with a predetermined maximum output level in an attempt to prevent ear damage. This approach is ineffective as it does not take into account listening duration and the calculation of risk for auditory injury. Other headphones are maximum-limited to produce levels that can still result in significant overexposure given enough time, or limit the user to levels, which may not be sufficient to achieve a short term listening level. In the latter case, consumer acceptance for the protective gear could be severely limited and a product would fail to survive in a competitive market and therefore be of no use.

Another alternative known in the art is to reduce the headphone output levels by increasing earphone impedance via an accessory placed between the media player and the earphones. The limitation of this approach is that it gives no consideration to the duration of exposure, and again either the user's chosen listening level cannot be achieved because the maximum level is too limited, or the level is sufficient to allow the user access to high enough sound levels, but risk overexposure due to potential duration of use.

Accordingly, a system that overcomes the shortcomings in the prior art would be useful.

BRIEF SUMMARY OF THE INVENTION

A system for monitoring sound pressure levels at the ear includes audio inputs for receiving ambient sounds and sounds received within the ear and outputting an audio input signal. An audio input level monitor receives the audio input signal and outputs a sound level signal corresponding to the strength of the audio input signal to a minimum threshold detector. The minimum threshold detector outputs a start signal if it has been determined that the sound level does not equal a minimum threshold level.

A digital timer receives the start signal and begins a clock until the minimum level threshold detector either receives a minimum level threshold sound level signal and discontinues output of the start signal or until the sound level pressure changes to another value, at which time a new start signal measuring a new time interval is output. The timer measures an amount of time during which the audio inputs have been exposed to a sound having a different level than the minimum threshold level. The elapsed time period is input to both a listening history database and to a listening fatigue calculator. The listening fatigue calculator receives an input from the digital timer and the input level detector and, as a function of the level of sound exposure and the time-period of exposure, determines a listening fatigue factor. When the listening fatigue factor corresponds to a state predictive of a damage level, the listening fatigue calculator outputs a warning to the system user of potential harm.

In at least one exemplary embodiment, this system includes an output acoustical transducer within the ear to reproduce the sound received at the ear. The system controls the level of noise produced in the ear as a function of the listening fatigue calculation. Additionally, ambient noise detection cancellation can be used to control the level of ambient noise. The warning of unsafe exposure to noise can include an audio warning at the ear, a visual warning in associated equipment, or one of attenuation or a complete noise cutoff at the output transducer.

In at least one exemplary embodiment, the audio input is disposed within an earpiece in situ in the ear for substantially occluding the ear. The system can also include an output transducer in the earpiece, which converts the input sound to a sound signal produced within the ear. The listening fatigue calculator attenuates the noise output by the output transducers upon receipt of the fatigue signal.

In at least one exemplary embodiment, the listening fatigue calculation is a function of the sound pressure level over time, the effective quiet level and exposure to the effective quiet level over time.

In still another exemplary embodiment, the listening fatigue calculation may also be a function of a noise reduction rate of the earpiece embodying the system as it processes the input audio signal to produce the output audio signal.

DETAILED DESCRIPTION OF THE INVENTION

Figure 1:
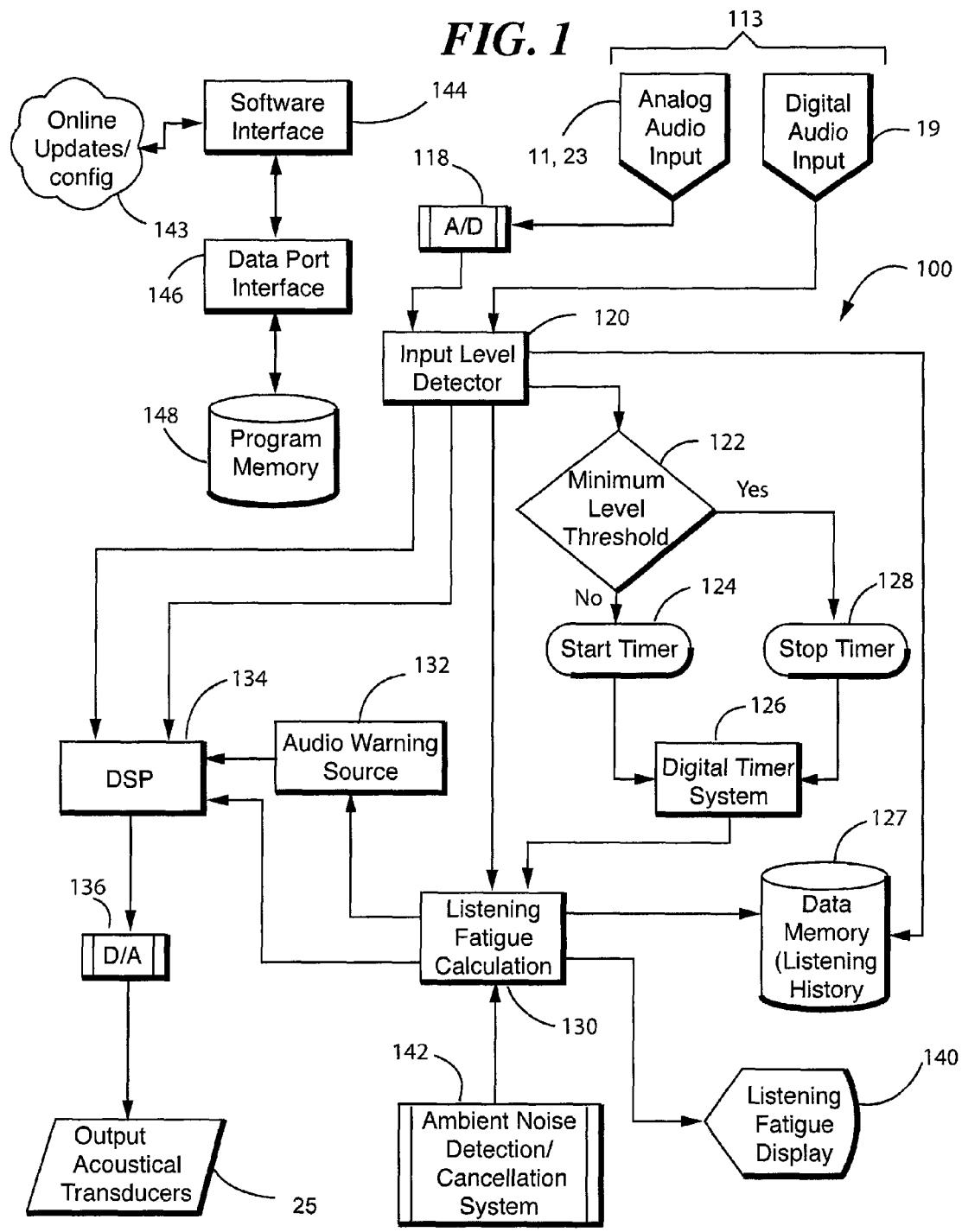
FIG. 1 is a block diagram of the system for measuring and determining exposure to sound over time at the ear constructed in accordance with a first exemplary embodiment of the invention.

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example the fabrication and use of transducers.

In all of the examples illustrated and discussed herein, any specific values, for example the sound pressure level change, should be interpreted to be illustrative only and non-limiting. Thus, other examples of the exemplary embodiments could have different values.

Note that similar reference numerals and letters refer to similar items in the following figures, and thus once an item is defined in one figure, it may not be discussed for following figures.

Note that herein when referring to correcting or preventing an error or damage (e.g., hearing damage), a reduction of the damage or error and/or a correction of the damage or error are intended.

Figure 2:
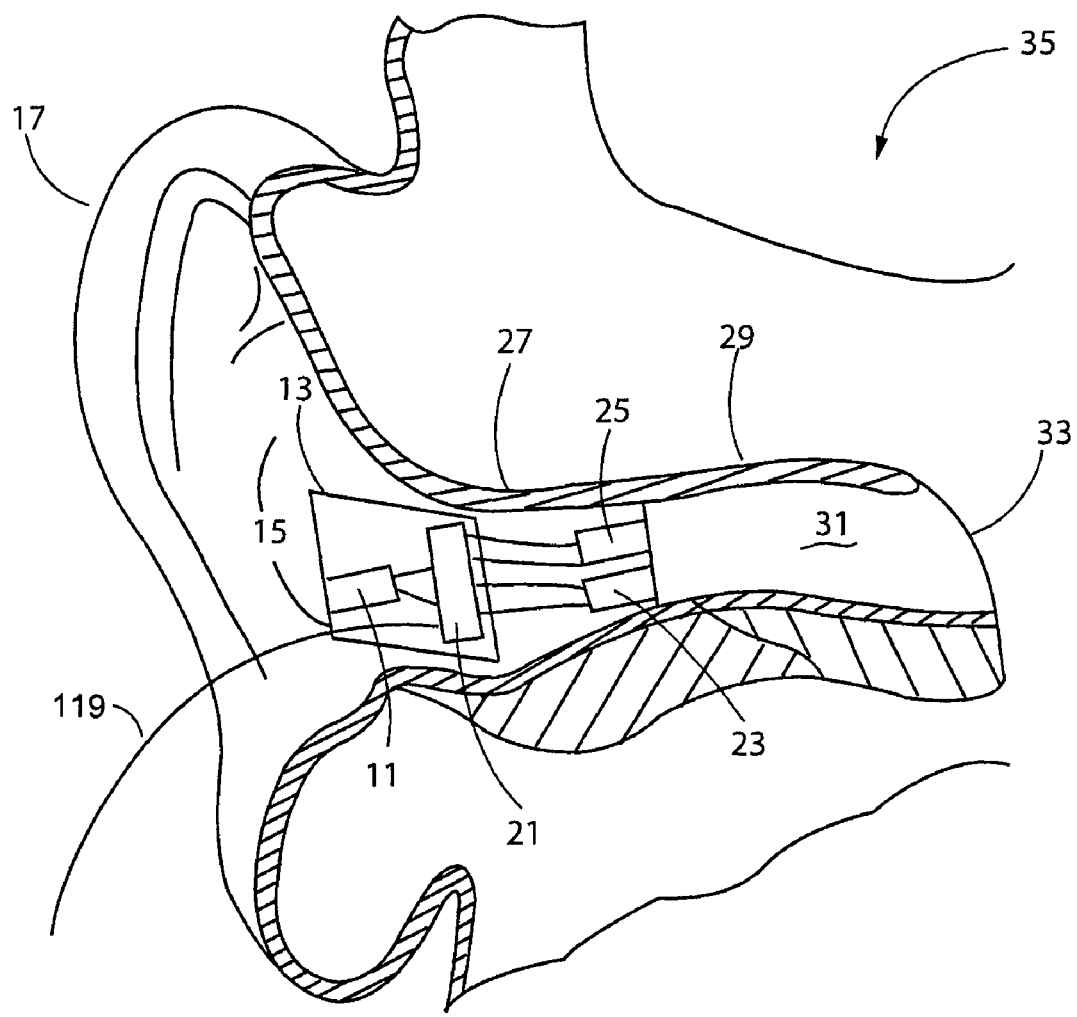
FIG. 2 is a block diagram of the system in accordance with at least one exemplary embodiment of the invention in situ in the ear.

At least one exemplary embodiment of the invention is directed to measuring and determining the exposure to sound at the ear over time. Reference is made to FIG. 1 in which a system, generally indicated as 100, is constructed in accordance with at least one exemplary embodiment of the invention. System 100 includes an audio input device 113 for receiving sound at the ear. As will be discussed below, audio input device 113 can include an analog audio input device 11, 23 and a digital audio input 19. In at least one exemplary embodiment, audio input 113 receives audio input from at least one of three sources, namely; ambient noise around the ear, direct input noise such as a MP3 player or other device which can produce a digital audio input at digital audio input 19, and noise as detected within the ear canal 31 (FIG. 2). The audio input device 113 outputs an audio signal corresponding to the received sound. Analog output signals from analog audio inputs 11, 23 are converted to a digital signal by an analog-to-digital (ND) converter 118 so that digital sound signals are input into an input level detector 120.

Input level detector 120 determines the sound pressure level of the sound received at audio input device 113. Input level detector 120 outputs a sound pressure level (SPL) signal, which is input to a minimum-level threshold detector 122. Minimum level threshold detector 122 determines whether or not the sound pressure level as detected by input level detector 120 exceeds a minimum level threshold. As will be discussed below, the minimum level threshold can be the effective quiet level of the individual, or some predetermined level substantially corresponding to a level which is ear damage neutral over time or a level of interest, such as 80 dB, because of its effect on the ear. Therefore, if the minimum level threshold is detected as being exceeded, a loud signal is output to a start timer 124, which triggers a digital timer system 126 to begin a clock. Conversely, if the minimum level threshold is detected as being below the minimum threshold, a quiet signal is output to a start timer 124, which triggers a digital timer system 126 to begin a clock of a restorative period. If the sound pressure level is at the minimum threshold, no clock needs to be started because this is neutral to the desired effect. In a preferred embodiment, the clock signal is changed with every significant (more than 1 dB by way of example) change in sound pressure level to get an accurate profile of sound exposure over time.

Once the sound pressure level as detected at input level detector 120 is at the minimum level, a stop timer signal is output from stop timer 128 to digital timer system 126 to stop the clock corresponding to exposure to the loud level. Digital timer system 126 outputs a clock value corresponding to the time period at which the minimum level threshold was not met, or in the proffered embodiment, for each period corresponding to a discrete level change.

A data memory or learning history databank 127 receives the clock value from digital timer system 126 as well as the actual input level detected at input level detector 120 and determines a listening history or sound pressure level exposure history. The sound pressure level exposure history is a record of the user's exposure to sound pressure levels over time. Because the effect of exposure is cumulative, it is important that the exposure history be maintained. The listening history, as will be discussed below, can include real ear level data, listening duration data, time between listening sessions, absolute time, sound pressure level dose data, including any restorative sound level, number of acoustic transients and crest factor and other data.

The sound pressure level exposure history or listening history includes both the listening habits history and the environmental or ambient noise exposure history. The environmental noise exposure history is the exposure of a user to environmental noise over time as a result of the auditory stimuli inherent to the environment where the user is present. This can be highway traffic, construction site, even the restorative effect of the quiet of a library whereas, the listening habits history is associated for the purposes for this disclosure with user-directed auditory stimuli such as music, words, other noises, which a user intentionally encounters for a purpose such as communication, learning, and enjoyment. Therefore, database 127, as will be discussed below, stores the cumulative SPL exposure.

It should be noted that in at least one exemplary embodiment, minimum level threshold detector 122 also starts the timer 124 when the sound pressure level is below the predetermined level. In this way, the restorative effect of below effective quiet noise is accumulated for determining overall exposure damage potential.

In effect, the only time that digital timer system 126 is not running is when the detected sound pressure level signal is at the minimum threshold level. A listening fatigue calculator 130 receives the input level signal from input level detector 120 and data from the data memory listening history 127, and determines whether or not listening fatigue or hearing damage is likely to occur as a result of further exposure. Hearing damage is the injury to the hearing mechanism including conductive and sensorineural decrement in hearing threshold levels. It can be either temporary or permanent so long as it is a result of the noise exposure above Effective Quiet. In other words, listening fatigue calculator 130 will output a signal when a threshold determined as a function of exposure time and sound pressure level, as will be discussed in greater detail below, is achieved. At that point, a listening fatigue signal is output.

It should be noted that in an alternative embodiment, system 100 can make use of an ambient noise detection/cancellation system 142 as known in the art. These systems produce signals, which negate noise pressure levels at certain frequencies and/or certain levels to reduce the effect of undesired noise, whether environmental noise or user directed noise. It will have some effect in elongating the exposure time by negating the sound pressure level detected by input level detector 120.

In at least one exemplary embodiment, the listening fatigue signal is utilized to prevent damage and encourages some action by the user when exposure levels are near damaging levels. Therefore, in one non-limiting example, a listening fatigue display 140 is provided for receiving the listening fatigue signal and displaying to the user a prompt to discontinue exposure to the sound level from the damaging sound source or audio source.

In another non-limiting example, the listening fatigue signal is output to an audio warning source 132, which outputs an output audio warning to the user notifying the user that exposure to the sound source has reached critical levels.

In at least one exemplary, but non-limiting, embodiment, as will be discussed below, system 100 includes an output acoustical transducer 25 to provide an audio signal to the ear. Output acoustical transducer 25 operates under the control of a digital signal processor (DSP) 134. Digital signal processor 134 receives a digital audio signal from input level detector 120, which acts as a pass through for the digitized signals from audio input device 113. Digital signal processor 134 passes the sound signals through to a digital to analog (D/A) converter 136 to drive acoustical transducers 25 to recreate the sound received at audio input device 113 inside the ear canal 31 in at least one exemplary embodiment of the invention as shown in FIG. 2. With such an exemplary embodiment, audio warning source 132 provides an output to digital sound processor 134 causing output acoustical transducer 25 to output a warning sound inside the ear of the user.

Lastly, in at least one further exemplary embodiment, listening fatigue calculator 130 outputs a listening fatigue signal to digital processor 134 which causes digital signal processor 134 to attenuate the sound signal prior to output to acoustical transducer 25 to reduce the signal output level by any of the linear gain reduction, dynamic range reduction, a combination of both, or a complete shutdown of transducer 25. Attenuation would be at least to the level, if not below, the effective quiet level to allow for ear recovery prior to damage.

It should be noted, that because personal hearing levels can change from person to person, and because both of the time intervals are a function of many variables, in a non-limiting example, to provide a dynamic ever-changing response, system 100 operates under software control. The configuration of the digital sound processor 134, listening fatigue calculator 130, the minimum level threshold detector 122, and the input level detector 120 are operated under software control.

In an exemplary embodiment of the invention, the control programs are stored in a program memory 148 for operating the firmware/hardware identified above. Furthermore, the program stored within memory 148 can be personalized as a result of testing of the user's ear, or by other modeling methods, in which system 100 includes a software interface 144 for receiving online or remote source updates and configurations. The software interface 144 communicates with a data port interface 146 within system 100, which allows the input of software updates to program memory 148. The updates can be transmitted across a distributed communications network, such as the Internet, where the updates take the form of online updates and configurations 143.

It should be noted that there is multiple functionality distributed across system 100. In at least one exemplary embodiment, at least audio input device 113 and acoustical transducer 25 are formed as an earpiece, which extends into the outer ear canal so that the processing of signals pertains to sound received at the ear. However, it is well within the scope of at least one exemplary embodiment of the invention to provide substantially all of the functionality in an earpiece so that system 100 is a "smart device."

Reference is now made to FIG. 2 in which system 100 in which the transducer configuration, that portion of system 100 which converts sound pressure level variations into electronic voltages or vice versa is shown. In this embodiment, acoustic transducers include microphones as an input and loudspeakers as an acoustical output.

FIG. 2 depicts the electro acoustical assembly 13 (also referred to herein as an in-the-ear acoustic assembly 13 or earpiece 13), as it would typically be placed in the ear canal 31 of ear 17 of user 35. The assembly is designed to be inserted into the user's ear canal 31, and to form an acoustic seal with the walls 29 of the ear canal 31 at a location 27, between the entrance 15 to the ear canal 31 and the tympanic membrane or eardrum 33. Such a seal is typically achieved by means of a soft and compliant housing of assembly 13. A seal is critical to the performance of the system in that it creates a closed cavity in ear canal 31 of approximately 0.5 cc in a non-limiting example between the in-ear assembly 13 and the ear's tympanic membrane 33.

As a result of this seal, the output transducer (speaker) 25 is able to generate a full range bass response time when reproducing sounds for the system user. This seal also serves to significantly reduce the sound pressure level at the user's eardrum 33 resulting from the sound field at the entrance 15 to the ear canal 31. This seal is also the basis for the sound isolating performance of the electroacoustic assembly 13. Located adjacent to speaker 25, is an ear canal microphone 23, which is also acoustically coupled to closed cavity 31.

One of its functions is that of measuring the sound pressure level in cavity 31 as a part of testing the hearing acuity of the user as well as confirming the integrity of the acoustic seal and the working condition of itself and speaker 25. Audio input 11 (also referred to herein as ambient sound microphone (ASM) 11) is housed in assembly 13 and monitors sound pressure at the entrance 15 to the occluded ear canal. All transducers receive or transmit audio signals to an ASIC 21 that undertakes at least a portion of the audio signal processing described above and provides a transceiver for audio via the wired or wireless communication path 119.

In the above description the operation of system 100 is driven by sound pressure level, i.e. sound levels are monitored for time periods or epochs during which the sound pressure level does not equal the minimum threshold or is constant. However, as will be discussed in connection with the next exemplary embodiments of the invention, system 100 can also operate utilizing fixed or variable sampling epochs determined as a function of one or more of time and changes in sound pressure level, sound pressure dosage level, a weighted sound pressure level, and restorative properties of the ear.

Figure 3:
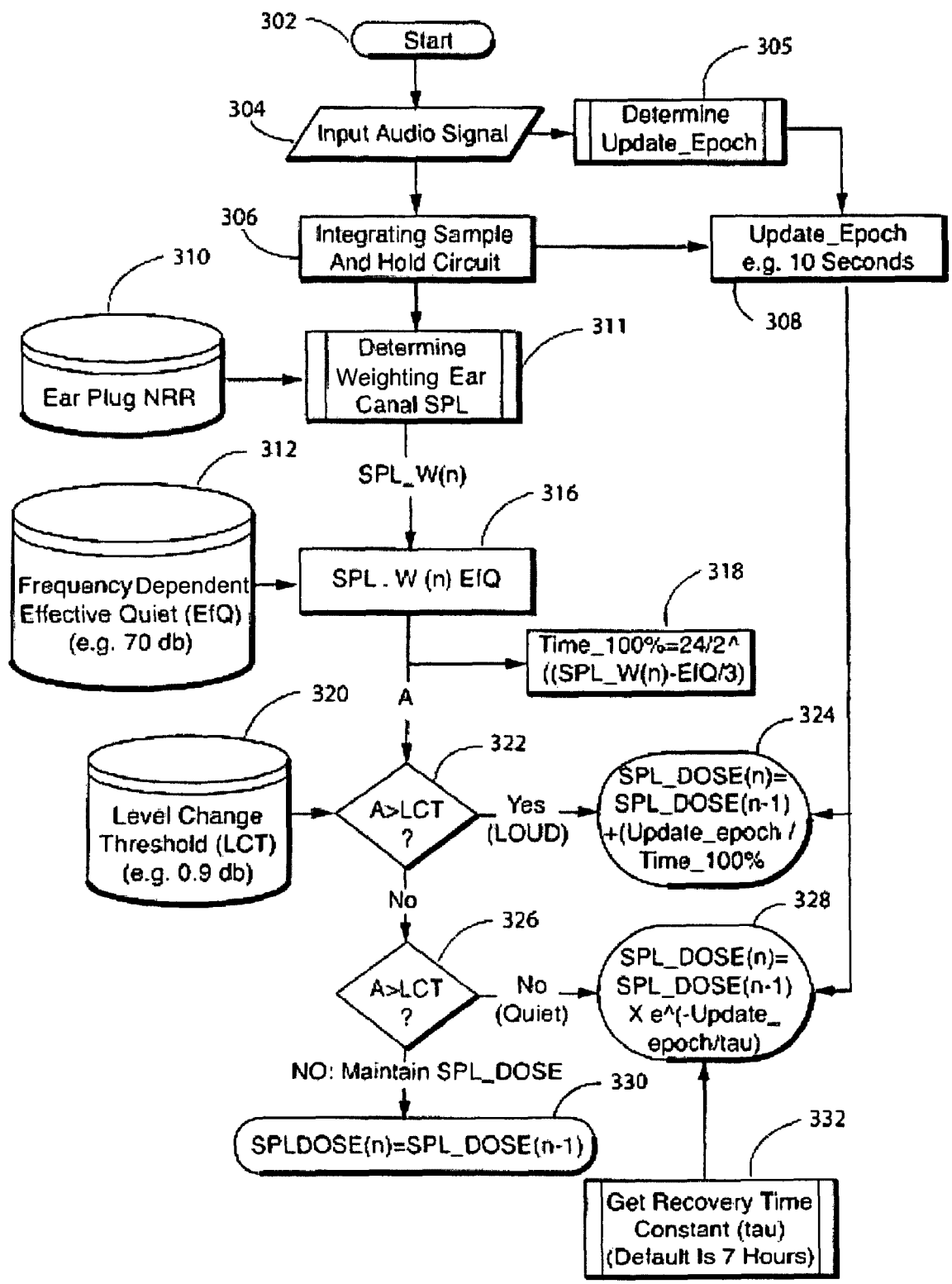
FIG. 3 is a flow chart for calculating listening fatigue in accordance with at least one embodiment of the invention by measuring a quantity (e.g., the sound pressure level) over time as perceived at the ear.

Reference is now made to FIG. 3 in which a flow chart for monitoring the sound pressure level dose at various sample times n is provided. The process is started in a step 302. An input audio signal is generated in a step 304 at either the ear canal microphone (ECM) 23 or the ambient sound microphone (ASM) 11. Exposure time is a function of the sound pressure level, therefore, the epoch or time period used to measure ear exposure or, more importantly, the time-period for sampling sound pressure level is determined in a step 305. The update epoch is used in the SPL dose function determination as well as to effect the integration period for the sound pressure level calculation that, as will be discussed below, is used to calculate the weighted ear canal sound pressure level.

Figure 6:
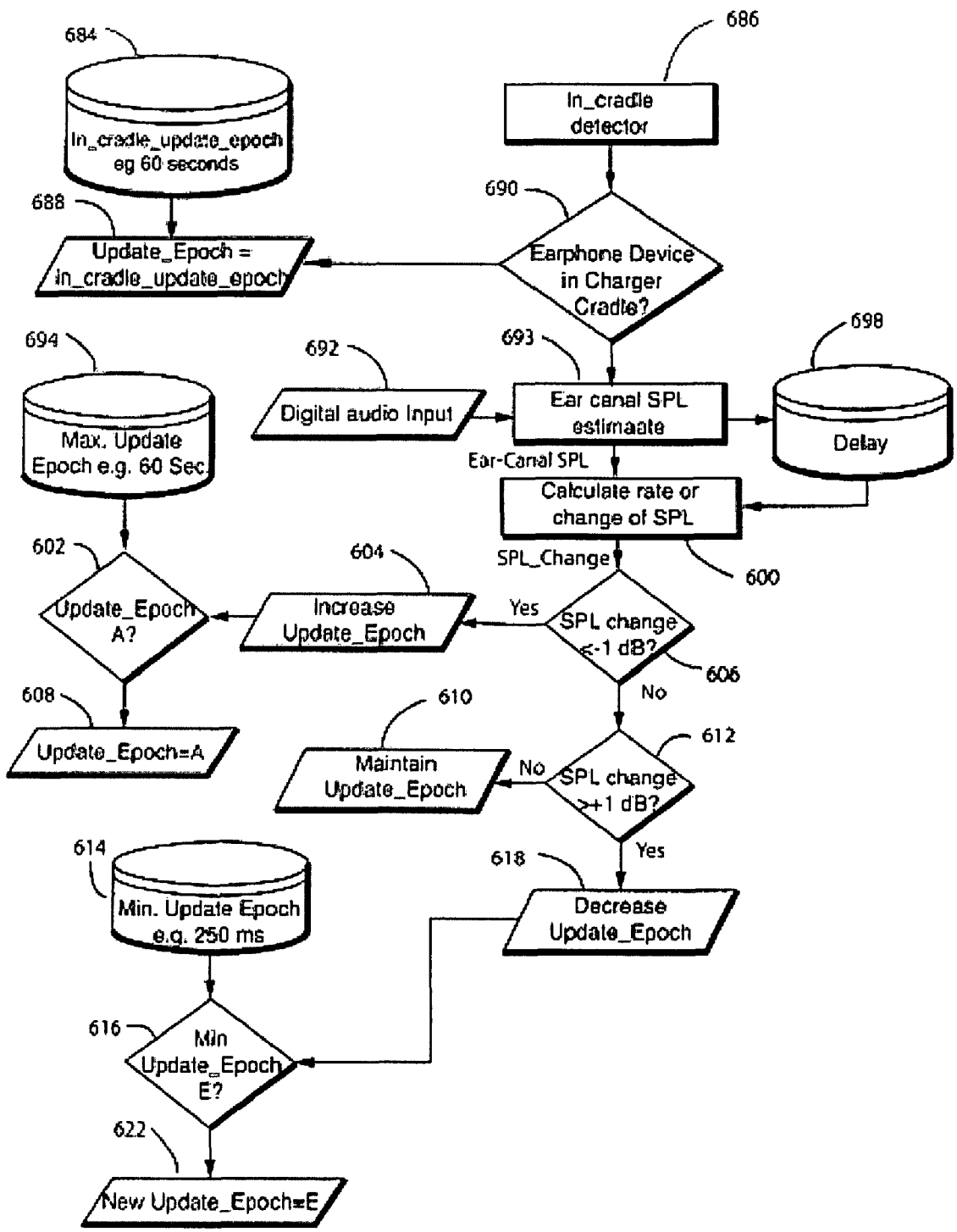
FIG. 6 is a flow chart for determining an update epoch in accordance with at least one exemplary embodiment of the invention.
Figure 7:
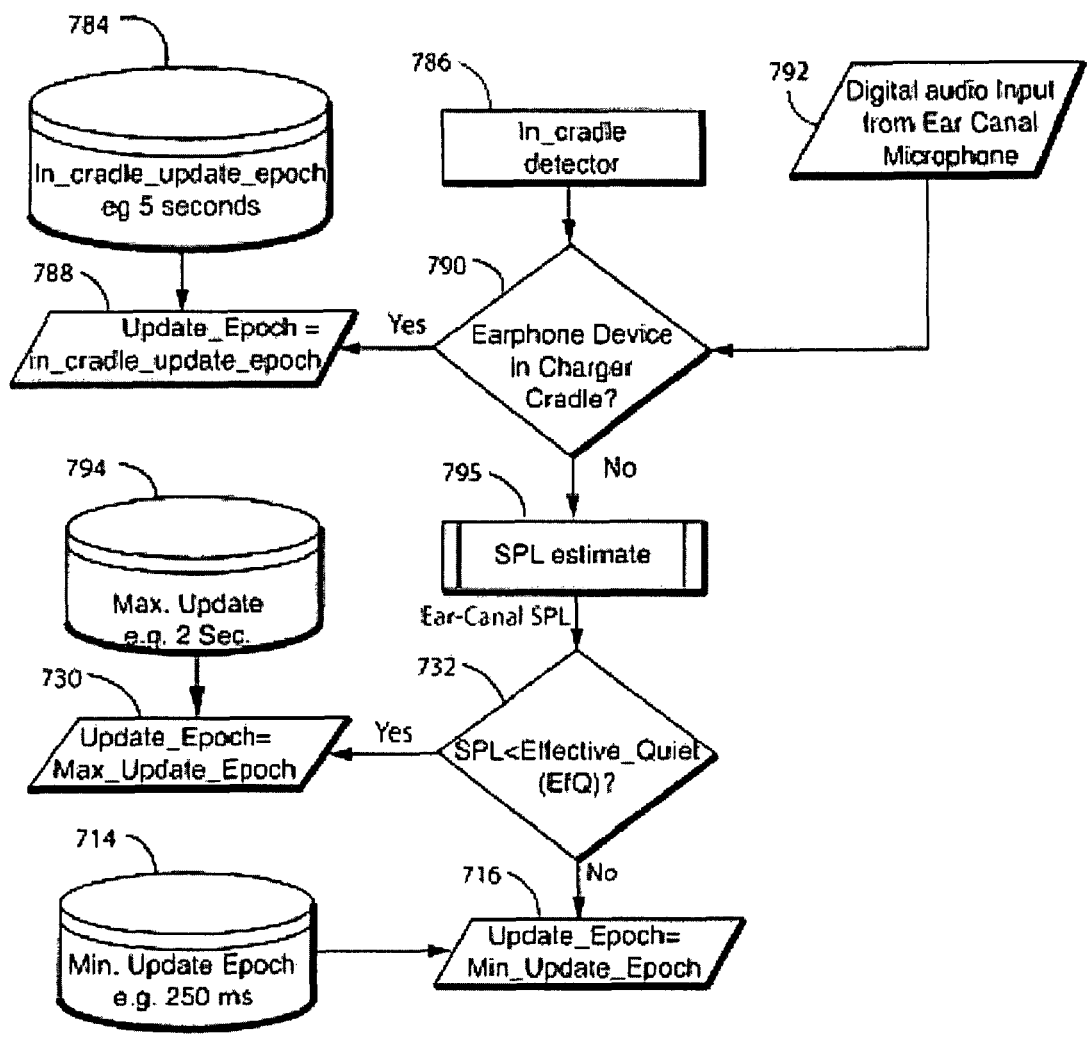
FIG. 7 is a flow chart for determining an update epoch in accordance with yet another exemplary embodiment of the invention.

Reference is now made to FIGS. 6 and 7. In FIG. 6, a method is defined to change the update epoch as a function of the weighted ear canal sound pressure level, which will be discussed in greater detail below. System 100 is capable of determining when earpiece 13 is in a charger or communication cradle (i.e., not in use in the ear of the user). In a step 684, a predetermined standard is provided for the update epoch, 60 seconds in this example. In step 688, the update epoch is set as the in-cradle update epoch. The in-cradle state is detected in step 686. If it is determined in a step 690 that earpiece 13 (also referred to herein as earphone device 13) is in a charger or cradle mode, then the update epoch is set as the in-cradle epoch; in the step 688.

However, if in step 690 it is determined that the earphone device 13 is in use, in other words "not in the cradle", then, by default, an audio signal is input to earpiece 13 in step 692. In step 693, an ear canal sound pressure level is estimated as a function of the audio input at step 692. The current (n) ear canal sound pressure level estimate is stored as a delay level in a step 698. An audio input is determined at a later time when step 692 is repeated so that a second in-time ear canal sound pressure level estimate is determined.

In a step 600, the delayed (n−1) or previous sound pressure level is compared with the current (n) ear canal sound pressure level estimate to calculate a rate of change of the sound pressure level. The change level is calculated in units of dB per second. This process of step 692 through 600 is periodically repeated.

In a step 606, it is determined whether or not the sound pressure level change is less than a predetermined amount (substantially 1 dB by way of non-limiting example) between iterations, i.e., since the last time the ear canal sound pressure level is calculated. If the change is less than the predetermined level, then in step 604 the update epoch is increased. It is then determined in a step 602 whether or not the epoch update is greater than a predefined amount D set in step 694 as a maximum update epoch such as 60 seconds in a non-limiting example. If in fact, the update epoch has a value greater than the maximum update epoch D then the update epoch is set at the higher value D in step 608.

If it is determined in step 606 that the sound pressure level change is greater than −1 dB, but less than +1 dB as determined in step 612, then the update epoch value is maintained in a step 610. However, if it is determined that the sound pressure level change is greater than +1 dB, then the update epoch value is decreased in a step 618 to obtain more frequent couplings. A minimum predetermined update epoch value such as 250 microseconds is set in a step 614. If the decreased update epoch determined in step 618 is less than, in other words an even smaller minimum time-period than the predetermined minimum update epoch E, then the new update epoch is set as the new minimum update epoch value in steps 616 and 622. In this way, the sample period is continuously being adjusted as a function of the change in sound pressure level at the ear. As a result, if the noise is of a spike variety as opposed to a constant value, the sampling interval will be changed to detect such spikes and protect the ear.

Reference is now made to FIG. 7 in which a method for changing the update epoch is illustrated as a function of the way that the ear canal sound pressure level estimate is provided. Again, in accordance with at least one exemplary embodiment of the invention, the update epoch is decreased when the ear canal sound pressure level is high or increasing.

The difference between the embodiment of FIG. 7 and the embodiment of FIG. 6 is that the update epoch is not continuously adjusted, but is more static. If the ear canal sound pressure level is less than effective quiet (a decibel level) which when exposed to the ear over time does not damage or restore the ear, then the update epoch is fixed at a predefined maximum epoch value and this is the value used by system 100 as will be discussed in connection with FIG. 3 below. In this embodiment, if the ear canal sound pressure level is determined to be greater then effective quiet, then the update epoch is fixed at a shorter minimum value and this is returned as the update epoch to be utilized.

In FIG. 7, specifically, as with FIG. 6, an in-cradle update epoch of 5 seconds by way of non-limiting example, is stored in system 100 in a step 784. In a step 788, the initial update epoch is set as the in-cradle update epoch. A maximum update epoch time, such as 2 seconds by way of non-limiting example, is stored in a step 794. In a step 714, an initial minimum update epoch (250 microseconds in this non-limiting example) is stored.

In a step 786 and step 790 it is determined whether or not system 100 is in a non-use state, i.e., being charged or in a cradle. If so, then the update epoch is set at the in-cradle update epoch. If not, then a digital audio signal is input from ear canal microphone 23 in step 792. A sound pressure level is estimated in step 795. It is then determined whether or not the ear canal sound pressure level is less than effective quiet in a step 732. If the sound pressure level is less than the effective quiet as determined in step 732, then the update epoch is set at the maximum update epoch in a step 730. If the sound pressure level is louder than the effective quiet, then in step 716, the update epoch is set to the minimum update epoch.

Returning to FIG. 3, in a non-limiting exemplary embodiment, the update epoch is set at 10 seconds in a step 302 utilizing either a constant predetermined sample time, or either of the methodologies discussed above in connection with FIGS. 6 and 7. In a step 306, the input audio signal is sampled, held, and integrated over the duration of the epoch as determined in step 308. As a result, the update epoch affects the integration period utilized to calculate the sound pressure level dose as a function of the sound pressure level and/or as the weighted ear canal sound pressure level.

In a step 310, an earplug noise reduction rate (NRR) is stored. The noise reduction rate corresponds to the attenuation effect of earpiece 13, or system 100, on sound as it is received at audio input 11 and output at the output transducer 25 or as it passes from the outer ear to the inner ear, if any exemplary embodiment has no ambient sound microphone 11. In a step 311, a weighting ear canal sound pressure level is determined, partially as a function of the earplug noise reduction rate value.

Figure 4:
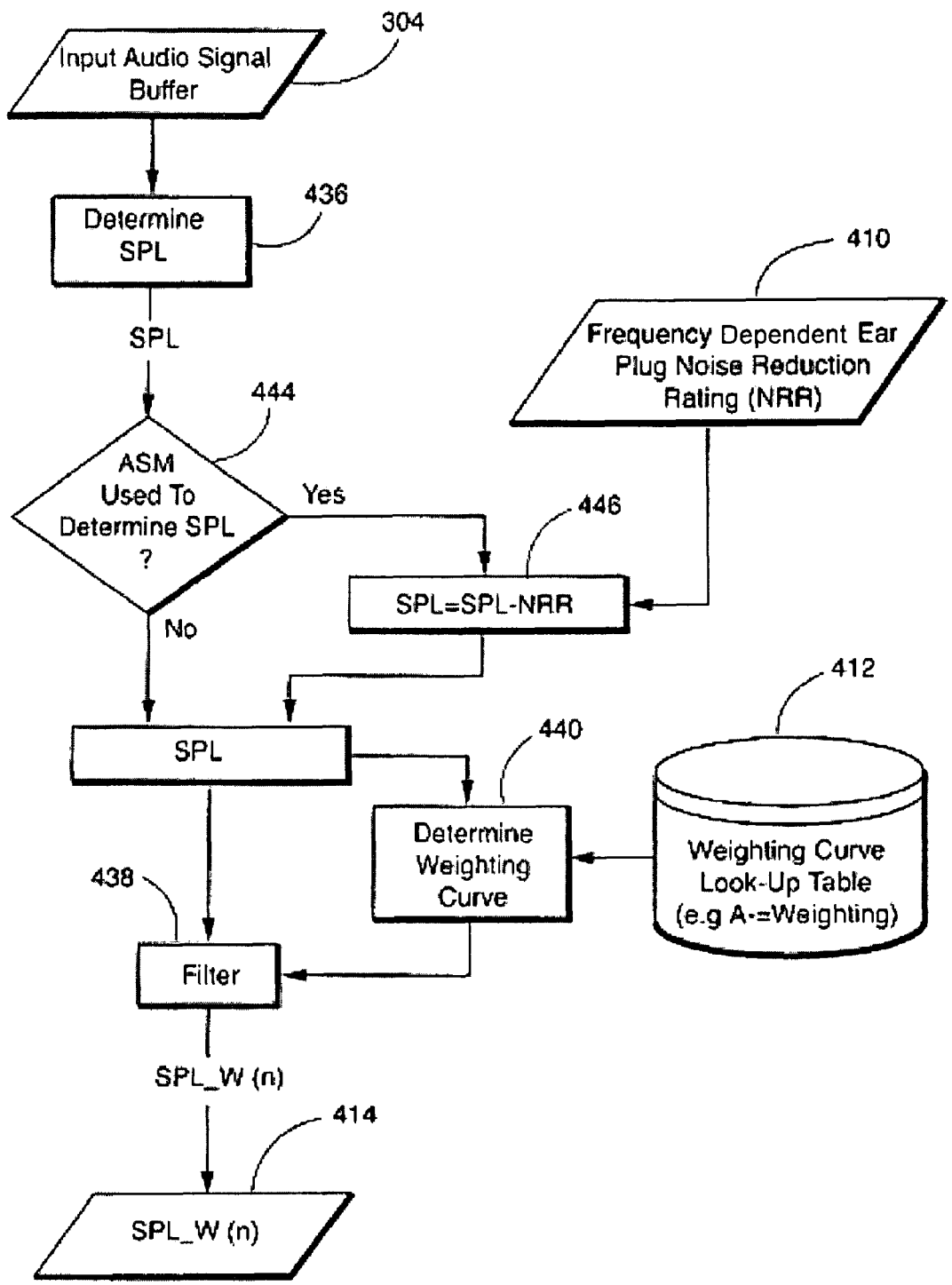
FIG. 4 is a flow chart for determining a weighted ear canal sound pressure level in accordance with another exemplary embodiment of the invention.

Reference is now made to FIG. 4 where a method for determining the weighted ear canal sound pressure level in accordance with at least one exemplary embodiment of the invention is illustrated. Like numerals are utilized to indicate like structure for ease of discussion and understanding. Weighting is done to compensate for the manner in which sound is perceived by the ear as a function of frequency and pressure level. As sounds get louder, the ear hears lower frequencies more efficiently. By weighting, if the level of the sound of the field is low, the methodology and system utilized by at least one exemplary embodiment of the invention reduces the low frequency and high frequency sounds to better replicate the sound as perceived by the ear.

Specifically, a weighting curve lookup table, such as A-weighting, acts as a virtual band-pass filter for frequencies at sound pressure levels. In a step 304, the audio signal is input. In step 410, frequency-dependent earplug noise reduction ratings are stored. These values are frequency-dependent and in most cases, set as manufacturer-specific characteristics.

As discussed above, in a step 306, the input audio signal is shaped, buffered and integrated over the duration of each epoch. The sound pressure level of the shaped signal is then determined in a step 436. It is determined whether or not ambient sound microphone 11 was utilized to determine the sound pressure level in a step 444. If microphone 11 was utilized, then the frequency-dependent earplug noise reduction rating of earpiece 13 must be accounted for to determine the sound level within the ear. Therefore, the noise reduction rating, as stored in step 310, is utilized with the sound pressure level to determine a true sound pressure level (at step 446) as follows:

$$SPL_{ACT}=SPL-NRR:$$

where sound pressure $SPL_{ACT}$ is the actual sound pressure level perceived at the ear, SPL is the sound pressure level determined in step 436 and NRR is the noise rate reduction value stored in step 410.

If the ambient sound microphone 11 is not used to determine the sound pressure level then the sound pressure level determined in step 436 is the actual sound pressure level. So that:

$$SPL_{ACT}=SPL$$

It is well within the scope of at least one exemplary embodiment of the invention to utilize the actual sound pressure level as determined so far to determine the affect of the sound pressure level sensed at the ear on the health of the ear. However, in at least one exemplary embodiment, the sound pressure level is weighted to better emulate the sound as heard within the ear. Therefore, in a step 412, a weighting curve lookup table is stored within system 100. In a step 440, the weighting curve is determined as a function of the actual sound pressure level as calculated or determined above in steps 436, 446 utilizing a weighting curve lookup table such as the A-weighting curve. The A-weighting curve is then applied as a filter in step 438 to the actual sound pressure level. A weighted sound pressure level for a sampled time period (SPL_W(n)) is obtained to be utilized in a step 414.

The weighting curve can be determined in step 440 by applying a frequency domain multiplication of the sound pressure level vector and the weighting curve stored in step 412. The weighting curves can be stored as a lookup table on computer memory, or can be calculated algorithmically. Alternatively, the input audio signal can be filtered with a time or frequency domain filter utilizing the weighting curve stored in step 412 and the sound pressure level as calculated. For low-level sound pressure levels, those less than 50 dB, by way of non-limiting example, a weighting curve, which attenuates low and high frequencies can be applied (similar to an A-weighting curve). For higher sound pressure levels, such as more than 80 dB, by way of non-limiting example, the weighting curve can be substantially flat or a C-weighting curve. The resulting weighted ear canal sound pressure level during any respective sampling epoch is returned as the system output SPL_W(n) in step 414.

Returning to FIG. 3, a safe listening time is calculated by comparing the weighted sound pressure level with the effective quiet level in step 316. Therefore, a value A corresponding to how far from safe listening the sound pressure level is, is determined by the equation:

$$A=SPL\_W(n)-EfQ$$

where EfQ is equal to the effective quiet time as stored at step 312.

By utilizing this simple comparative function, fewer machinations and processes are needed. System 100 takes advantage of the fact that because the effective quiet time is neutral to the ear, sound pressure levels significantly above the effective quiet level are generally damaging and noise levels below the effective quiet are generally restorative.

In a step 318, the remaining safe listening time at the beginning of any current sampling epoch (Time_100%) is calculated. The remaining safe listening time is calculated as follows:

$$\text{Time\_100\%}=24/2*((SPL\_W(n)-EfQ/3).$$

In this embodiment, rather than make use of the Sound Level (L), the period is a function of the loudness and quietness of the weighted sound pressure level. It should be noted that effective quiet is used in the above example, but any level of interest, such as 80 dB, or no sound level, i.e., SPL_W(n)–0, may be used. The weighted sound pressure level and effective quiet can be expressed as a frequency-dependent numerical array or a value scalar.

It is next determined whether or not the difference between the current weighted sound pressure level and the effective quiet is above a tolerable threshold or not, i.e., whether the weighted SPL in the eardrum is considered loud or not. A sound pressure level dose is calculated depending upon whether the sound level is loud or not. The sound pressure level dose is the measurement, which indicates an individual's cumulative exposure to sound pressure levels over time. It accounts for exposure to direct inputs such as MP3 players, phones, radios and other acoustic electronic devices, as well as exposure to environmental or background noise, also referred to as ambient noise. The SPL dose is expressed as a percentage of some maximum time-weighted average for sound pressure level exposure.

Because the sound pressure level dose is cumulative, there is no fixed time-period for ear fatigue or damage. At effective quiet, the sound pressure level exposure time would theoretically be infinite. While the time period for the sound pressure level dose becomes smaller and smaller with longer exposure to loud noise. A tolerable level change threshold corresponding to the amount of noise above or below the effective quiet which has no great effect on the ear as compared to effective quiet is determined and stored in memory 127 in a step 320. In a step 322, the differential between the weighted sound pressure level and the effective quiet is compared to the level change threshold.

A differential value A, corresponding to the level change, is calculated as follows:

$$A = SPL\_W(n) - EfQ$$

If A is greater than the level change threshold, the noise is considered loud and the sound pressure level is calculated in a step 324 as follows:

$$SPL\ Dose = SPL\ Dose(n-1) + (Update\_Epoch/Time\_100\%)$$

where SPL Dose(n−1) is the SPL Dose calculated during the last epoch;

Update_Epoch is the time (in hours) since the last SPL Dose was calculated. As described above, Update_Epoch can be adaptive, e.g., shortened when the sound pressure level is louder; and Time_100%, the time period remaining for safe exposure is determined by the equation:

$$Time\_100\% = 24\ hours/2^{((L-EfQ)/3)}$$

where L=sound level (in dB) of the combination of environmental noise and audio playback. It should be noted that sound level (L) can be substituted for SPL_W(n).

It should be noted, as can be seen from the equation, that the time value becomes more important than the sound pressure level as updates are spread apart. However, this is to protect overexposure to harmful sounds because a less accurate sample size must account for the unknown. The wider the periodicity, the less accurate determination of actual exposure. Infrequent updates of the dose assume a relatively constant sound level, ignoring spikes and intervening restorative periods. Accordingly, sound pressure level and epoch periodicity are weighed against each other to protect the ear.

If in step 322 it is determined that the differential is not greater than the level change threshold, including negative values for A (which are restorative values), then in step 326 it is determined whether or not the differential, as determined in step 316, is less than the level change threshold in a step 322. If it is determined that the differential is not less than the level change threshold, then the received noise was the effective quiet level, i.e., the level change threshold equals zero and in a step 330, the current SPL Dose is maintained at the same level. There is no change to the dose level. However, if the differential A is less than the level change threshold then this is a restorative quiet as determined in step 326, so the SPL dose is determined in a Step 328 as follows:

$$SPL\ Dose = SPL\ Dose(n-1) * e^{(-Update\_epoch/\tau)}$$

Where: τ (referred to as "tau" in the following diagrams) is equal to approximately 7 hours. In some embodiments, tau is adaptive for different users. In at least one exemplary embodiment, the level change threshold is set at substantially 0.9-1.0 dB.

In step 332, the recovery time constant tau is determined. It is not a function of exposure, but rather of recovery. It can be a default number or be determined as will be discussed below. As the SPL Dose is calculated by system 100, it is also monitored. Once the SPL Dose reaches a certain level, as it is a cumulative calculation, ear fatigue calculator 130 determines whether or not the SPL Dose corresponds to a fatigued ear, and if so, it outputs warnings as discussed in connection with FIG. 1.

Figure 5:
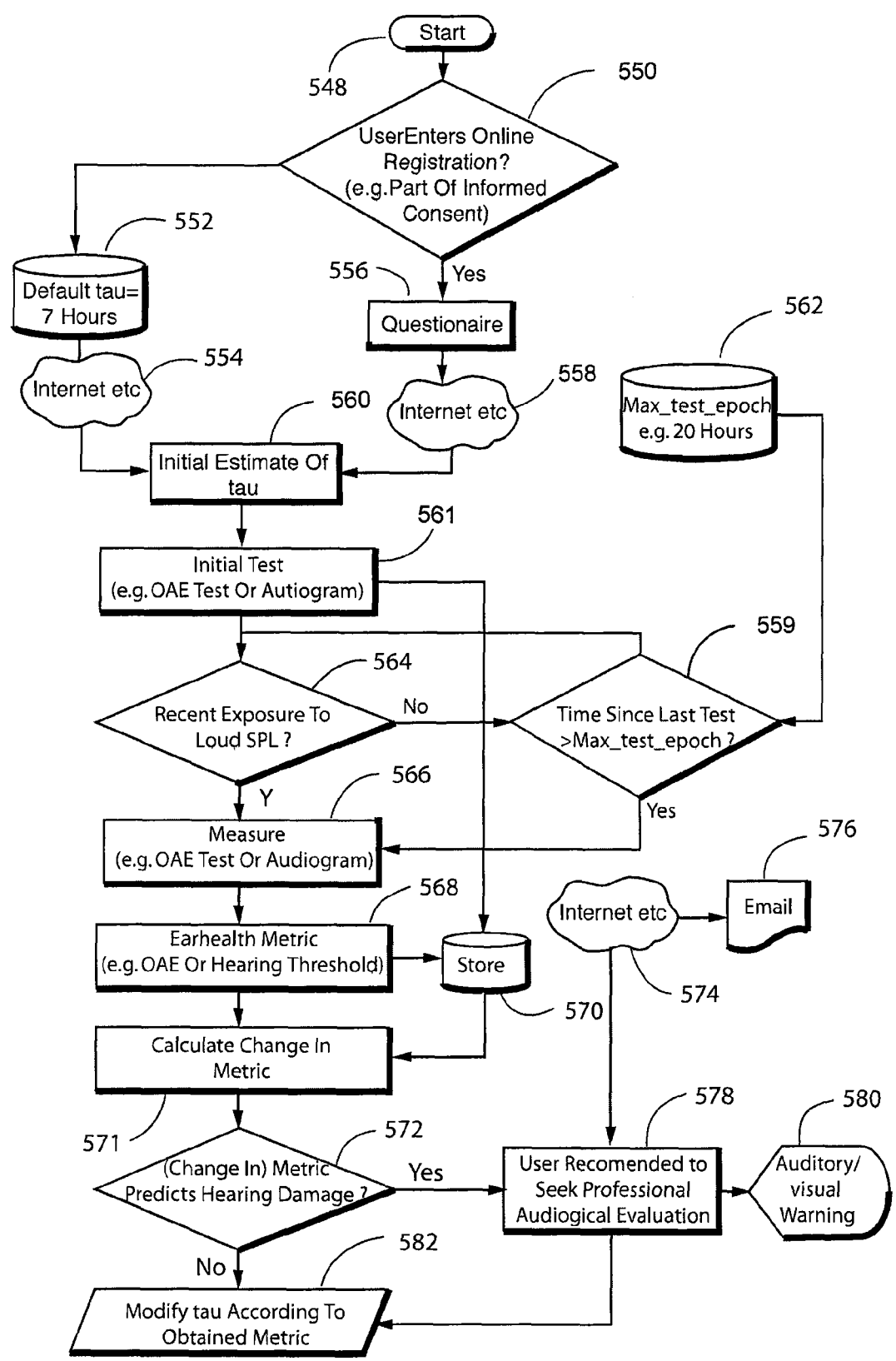
FIG. 5 is a flow chart for determining a personalized recovery time constant in accordance with another exemplary embodiment of the invention.

Reference is now made to FIG. 5 which depicts an optional methodology for not only updating the recovery time constant (tau) for individual users, but to provide additional methods for acting upon detected damaging exposure. The process is started at a step 548. In a step 550, it is determined whether or not the user wishes to make use of a registration process, for example online, for setting a personalized update epoch through communication with a remote registration system. If the user declines the registration, then the default tau is set at 7 hours in a step 552. In a step 554, this default value is transmitted to system 100 via a wired or wireless data communication network.

Alternatively, if the user registers in step 550, a questionnaire is presented in a step 556 in which the user informs system 100 regarding a user sound exposure history, age, work habits and other personal details that could affect the user's personal recovery function time, i.e., the time constant tau. The individual characteristics can be input to a formula or utilized as part of a look up table to determine the tau for the individual user. The estimate of tau determined in step 556 is transmitted to system 100 via a wireless or wired data communication system in a step 558. In step 560, the initial estimate of tau is set from the value determined in step 556 (or step 552).

An initial hearing test is performed in a step 561, which acquires data indicative of the user's hearing sensitivity. The test may be an otoacoustic emission (OAE) test or audiogram administered utilizing the ear canal receiver or speaker 25. However, the test can also be administered over the Internet, telephone or other communication device capable of outputting sounds sent across a distributed network and enabling responsive communication. The data is stored in a computer memory as an initial test value in a step 570 and is used in further processing to detect a change in the user hearing response.

In a step 564, it is determined whether the user has been recently exposed to loud sound pressure levels. This can be done utilizing the sound pressure level dose as stored or permanently calculated by system 100. If it is decided in step 564 that the user's ear canal sound pressure level is low, then in a step 559 it is determined whether the time since the last test is greater than a maximum test epoch. At the outset, the maximum test epoch is a set number determined in a step 562. In this non-limiting example, the maximum test epoch is set at 20 hours.

If it is determined that the time since the last test is greater than the maximum test epoch or, that there has been recent exposure to loud sound pressure level, then another test is administered in a step 566. The resulting test metrics are stored in steps 568, 570. In a step 571, the newly determined test metrics are compared to the initial test metrics to calculate any change in the metrics. In step 572, it is determined whether the change is predictive of hearing damage. If not, then in a step 582, the tau is modified according the obtained metric.

If it is determined that the hearing damage is predicted, then in a step 578 the user is recommended to remove themselves from the noise as discussed above with the operation of listening fatigue calculator 130 and furthermore, the user can be recommended to seek professional audiological evaluation in a step 578. This could be done by an in situ auditory or visual warning in step 580 by system 100. On the other hand, if system 100 is used in connection with a communications device such as a telephone or a personal digital assistant, an e-mail can be created in steps 574, 576; not only warning the user of potential damage, but notifying a health professional so that a follow up examination can be performed.

It should be noted that a change in the hearing metric (e.g., a hearing sensitivity curve) is measured by system 100. In response to the user's hearing metric, the recovery time constant tau is updated. For example, tau is shortened if the change in the user's hearing metric indicates the user has "sensitive ears", i.e., if, following loud sound exposure, the user's hearing sensitivity takes longer than seven hours to return to the individual's normal. This modified tau can be used to calculate the sound pressure level dose, in particular in a restorative phase, to determine better overall sound pressure level exposure.

By providing a monitoring and protective system which, in at least one mode, continuously monitors sound pressure level at the ear until a potentially harmful exposure has occurred, rather than only monitoring for a predetermined time as with noise dose monitors which monitor for work shifts, a more accurate predictor of harm to the ear is provided. By utilizing a method, which determines exposure in part as a function of effective quiet exposure as well as loud noise exposure, an enhanced model of potential risk is achieved. By providing a series of warning mechanisms and preventive measures as a function of the determined potentially harmful dosage levels ear damage is more likely to be prevented. By providing the system in an earpiece which substantially occludes the ear and making use of audio inputs at the external and internal ear, a more accurate reading of noise level is provided and more control through a real time warning system is achievable.

It should be known that values for level change threshold, effective quiet time, and epoch were used above as examples. However, it should be noted that any values which when input and utilized in accordance with the methodologies above prevent permanent damage to the ear are within the scope of the invention and the invention should not be so limited to the specific examples above.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, although specific numbers may be quoted in the claims, it is intended that a number close to the one stated is also within the intended scope, i.e., any stated number (e.g., 80 dB) should be interpreted to be "about" the value of the stated number (e.g., about 80 dB).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method for monitoring a sound pressure level at an ear comprising:
   receiving a sound at the ear;
   converting the sound into an input audio signal;
   sampling a sound pressure level of the input audio signal during an epoch including a plurality of time samples;
   determining whether the sound pressure level is at a minimum threshold;
   determining a current sound pressure level dose as a function of the sound pressure level sampled during the epoch;
   determining a cumulative sound pressure level dose as a function of the current sound pressure level dose and a previous sound pressure level dose; and
   adjusting a duration of the epoch based on the sampled sound pressure level to form an update epoch,
   wherein the duration of the epoch is:
      decreased when a rate of change of the sampled sound pressure level is greater than a predetermined threshold or the sampled sound pressure level is greater than the minimum threshold, to decrease a number of the time samples during the update epoch, and
      increased when the rate of change of the sampled sound pressure level is less than the predetermined threshold or the sampled sound pressure level is less than the minimum threshold, to increase the number of the time samples during the update epoch.

2. The method of claim 1, further comprising the step of outputting a warning when the cumulative sound pressure level dose reaches a predetermined level.

3. The method of claim 2, wherein said predetermined level corresponds to a level that is predictive of damage to the ear if further exposure to the sound is continued.

4. The method of claim 1, further comprising the step of determining whether the sound pressure level exceeds the minimum threshold, and wherein the cumulative sound pressure level dose is further determined as a function of the update epoch and a time period remaining for safe exposure when the sound pressure level exceeds the minimum threshold.

5. The method of claim 1, wherein the update epoch is determined as a function of a change in the sound pressure level between a first sample of the sound pressure level and at least a second sample of the sound pressure level.

6. The method of claim 1, wherein the sound pressure level is a weighted sound pressure level.

7. The method of claim 1, wherein the sound pressure level is a function of a noise rate reduction.

8. The method of claim 1, further comprising the step of determining whether the sound pressure level is less than the minimum threshold, and wherein the cumulative sound pressure level dose is a function of the previous sound pressure level dose and the update epoch when the current sound pressure level dose is less than the minimum threshold.

9. The method of claim 8, wherein the update epoch is a function of a recovery time for the ear.

10. The method of claim 9, wherein the recovery time is a preset value.

11. The method of claim 1, wherein the update epoch is a function of a rate of change in sound pressure level between a first epoch and at least a second epoch.

12. A method for monitoring a sound pressure level at an ear comprising:
   receiving a sound at the ear;
   converting the sound into an input audio signal;
   sampling a sound pressure level of the input audio signal during an epoch;
   determining whether the sound pressure level is less than a minimum threshold;
   determining a current sound pressure level dose as a function of the sound pressure level sampled during the epoch;
   determining a cumulative sound pressure level dose as a function of the current sound pressure level dose and a previous sound pressure level dose, wherein the cumulative sound pressure level dose is a function of the previous sound pressure level dose and an update epoch when the current sound pressure level dose is less than the minimum threshold, the update epoch being a function of a recovery time for the ear; and performing a hearing test on the ear, setting the recovery time as a function of a result of the hearing test.

13. The method of claim 12, wherein the hearing test is performed over a network.

14. The method of claim 13, wherein the hearing test comprises the steps of providing a questionnaire to a test subject; and receiving a response to the questionnaire by the test subject via the network.

15. The method of claim 13, wherein the hearing test determines a metric indicative of at least one of ear sensitivity and ear recovery time.

16. The method of claim 15, further comprising the steps of storing a result of the hearing test; conducting a subsequent hearing test; and comparing a result of the subsequent hearing test to the result of the hearing test; and calculating a change in the metric; and changing the recovery time as a function of the change in the metric.

17. The method of claim 16, further comprising the step of determining whether the change in the metric predicts potential hearing damage.

18. The method of claim 17, further comprising the step of notifying a subject being monitored of the potential hearing damage.

19. The method of claim 17, further comprising the step of providing a notice to a healthcare provider associated with a user being monitored.

20. The method of claim 18, wherein the notifying includes at least one of an e-mail, an auditory warning, and a visual warning.

* * * * *